United States Patent [19]
Rebstock et al.

[11] 4,128,540
[45] Dec. 5, 1978

[54] PYROGLUTAMYL-HISTIDYL-TRYPTOPHANYL-SERYL-TYROSYL HYDRAZIDES

[75] Inventors: Mildred C. Rebstock; Ernest D. Nicolaides; Thomas F. Mick; Francis J. Tinney; Eugene L. Wittle, all of Ann Arbor, Mich.

[73] Assignee: Parke, Davis & Company, Detroit, Mich.

[21] Appl. No.: 257,000

[22] Filed: May 25, 1972

[51] Int. Cl.$^2$ ........................................... C07C 103/52
[52] U.S. Cl. ..................... 260/112.5 R; 260/112.5 LH
[58] Field of Search ................................ 260/112.5 R

[56] References Cited

U.S. PATENT DOCUMENTS

| | | | |
|---|---|---|---|
| 3,778,427 | 12/1973 | Flouret | 260/112.5 |
| 3,780,014 | 12/1973 | Flouret | 260/112.5 |
| 3,781,272 | 12/1973 | Flouret | 260/112.5 |
| 3,784,535 | 1/1974 | Flouret | 260/112.5 |
| 3,787,385 | 1/1974 | Folkers et al. | 260/112.5 |
| 3,787,386 | 1/1974 | Flouret et al. | 260/112.5 |
| 3,790,554 | 2/1974 | Flouret | 260/112.5 |
| 3,790,555 | 2/1974 | Flouret et al. | 260/112.5 |
| 3,796,697 | 3/1974 | Flouret | 260/112.5 |

OTHER PUBLICATIONS

Baba et al., Biochem. Biophys. Res. Comm., 44, 459 (1971).
Matsuo et al., Biochem. Biophys. Res. Comm., 43, 1334 (1971).
Burgus et al., C.R. Acad. Sci. Paris, 273, Ser. D, 1611 (1971).
M. Bodanszky and M. Ondetti, "Peptide Synthesis", Interscience, New York (1966), pp. 75-81.
Merrifield, Adv. in Enzymology, 32, 243-244 (1969).

Primary Examiner—Delbert R. Phillips
Attorney, Agent, or Firm—Stephen Raines; David B. Ehrlinger; Frank S. Chow

[57] ABSTRACT

A new decapeptide having the formula, pGlu-His-Trp-Ser-Tyr-Gly-Leu-NO$_2$Arg-Pro-Gly(NH$_2$); salts thereof; production thereof by reacting pGlu-His-Trp-Ser-Tyr(N$_3$) with Gly-Leu-NO$_2$Arg-Pro-Gly(NH$_2$), by reacting pGlu-His-Trp-Ser-Tyr-Gly(N$_3$) with Leu-NO$_2$Arg-Pro-Gly(NH$_2$), or by reacting pGlu-His-Trp-Ser-Tyr-Gly-Leu(N$_3$) with NO$_2$Arg-Pro-Gly(NH$_2$); certain peptide intermediates and their salts used in the production thereof; and the use thereof in the preparation of luteinizing hormone releasing factor.

4 Claims, No Drawings

PYROGLUTAMYL-HISTIDYL-TRYPTOPHANYL-SERYL-TYROSYL HYDRAZIDES

SUMMARY AND DETAILED DESCRIPTION

The present invention relates to new peptide compounds that are useful as chemical intermediates and to methods for their production. More particularly, the invention relates to a new decapeptide that is represented by the formula

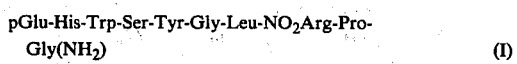

pGlu-His-Trp-Ser-Tyr-Gly-Leu-NO$_2$Arg-Pro-Gly(NH$_2$)     (I)

to salts thereof and to peptide intermediates and their salts employed in the production thereof. In formula I the conventional symbols for amino acid residues of peptide compounds are used and each is intended to have the following meaning: pGlu, L-pyroglutamyl; His, L-histidyl; Trp, L-tryptophanyl; Ser, L-seryl; Tyr, L-tyrosyl; Gly, glycyl; Leu, L-leucyl; NO$_2$Arg, N$^G$-nitro-L-arginyl; and Pro, L-prolyl. Thus, the decapeptide represented by formula I is named L-pyroglutamyl-L-histidyl-L-tryptophanyl-L-seryl-L-tyrosylglycyl-L-leucyl-N$^G$-nitro-L-arginyl-L-prolyl-glycinamide. The decapeptide of formula I can also conveniently be referred to as nitro-LRF, because of its relationship to the luteinizing hormone releasing factor (LRF), as explained in detail hereinafter. The symbols for amino acid residues used in formula I will also be used in the formulas that follow for other peptide compounds and each such symbol should be understood to have the meaning given above.

In accord with the invention, nitro-LRF is produced by reacting a peptide azide compound that is represented by the formula pGlu-His-Trp-Ser-R$_1$(N$_3$)     (II)

with a peptide compound that is represented by the formula

R$_2$-Pro-Gly(NH$_2$)     (III)

in a non-reactive solvent medium; where R$_1$ represents Tyr, Tyr-Gly, or Tyr-Gly-Leu, and R$_2$ represents Gly-Leu-NO$_2$Arg, Leu-NO$_2$Arg, or NO$_2$Arg. R$_1$ and R$_2$ are chosen in such a way that the final product of the reaction is in each case the decapeptide, nitro-LRF. Thus, when R$_1$ is Tyr, R$_2$ is Gly-Leu-NO$_2$Arg; when R$_1$ is Tyr-Gly, R$_2$ is Leu-NO$_2$Arg; and when R$_1$ is Tyr-Gly-Leu, R$_2$ is NO$_2$Arg.

The preferred solvent medium for the reaction between the peptide azide compound of formula II and the peptide for formula III is N,N-dimethylformamide, although a mixture of this solvent with dimethyl sulfoxide can also be used. The reaction is best carried out at a temperature between −25° and 10° C.; higher temperatures should be avoided in order to minimize undesirable side reactions. At a temperature in the indicated range, the reaction is normally essentially complete after a period of from 12 to 24 hours, but may advantageously be carried out for longer periods, up to 100 hours, to insure completeness of reaction. Equivalent amounts of the two peptide reactants are employed. The peptide compound of formula III may be used initially in free base or in hydrohalide salt form; when used in hydrohalide salt form, a tertiary amine base, such as triethylamine or N-methyl- or N-ethylmorpholine, is added to the reaction mixture in sufficient quantity to neutralize the salt.

The peptide azide compound of formula II above that is used as a reactant in the foregoing process is normally prepared in situ by reacting a peptide hydrazide compound represented by the formula

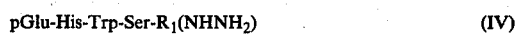

pGlu-His-Trp-Ser-R$_1$(NHNH$_2$)     (IV)

where R$_1$ has the same meaning as given above, with isoamyl nitrite in the presence of an acid in the chosen solvent medium, and is reacted further as described above without isolation. The preferred acid for use in the azide preparation is a solution of hydrogen chloride in tetrahydrofuran; between 3 and 6 equivalents of acid are used for each equivalent of the hydrazide of formula IV. The preparation of the azide is carried out at a temperature between −60° and 10° C. Following the in situ formation of the peptide azide of formula II, a tertiary amine such as triethylamine is added to the reaction mixture to neutralize the acid used, prior to the further reaction of the peptide azide with the peptide compound of formula III to form the nitro-LRF decapeptide product.

The peptide hydrazide compounds of formula IV above, which are also novel chemical intermediates of the present invention, are prepared by various methods. L-Pyroglutamyl-L-histidyl-L-tryptophanyl-L-seryl-L-tyrosyl hydrazide, that is, the pentapeptide hydrazide of formula IV wherein R$_1$ is Tyr, is prepared by the following series of reactions. pGlu-His(NHNH$_2$) is reacted with isoamyl nitrite in the presence of hydrogen chloride to give pGlu-His(N$_3$), which is reacted without isolation with L-tryptophane methyl ester hydrochloride [Trp(OMe)HCl] in the presence of triethylamine to give pGlu-His-Trp(OMe). The pGlu-His-Trp(OMe) intermediate is next reacted with hydrazine hydrate in methanol to give pGlu-His-Trp(NHNH$_2$), which in turn is converted into pGlu-His-Trp(N$_3$) in the usual way, and the tripeptide azide intermediate is further reacted with L-seryl-L-tyrosine methyl ester hydrochloride [Ser-Tyr(OMe)HCl] in the presence of base to give pGlu-His-Trp-Ser-Tyr(OMe), which is finally reacted with hydrazine hydrate, preferably in a lower alkanolic solvent, to give the desired pGlu-His-Trp-Ser-Tyr(NHNH$_2$) intermediate. The Ser-Tyr(OMe)HCl intermediate used in this procedure is obtained from the catalytic hydrogenation of N-benzyloxycarbonyl-L-seryl-L-tyrosine methyl ester that is represented by the formula

Z$_1$-Ser-Tyr(OMe)     (V)

where Z$_1$ represents benzyloxycarbonyl, in the presence of hydrogen chloride.

L-Pyroglutamyl-L-histidyl-L-tryptophanyl-L-seryl-L-tyrosylglycyl hydrazide, that is, the hexapeptide hydrazide of formula IV wherein R$_1$ is Tyr-Gly, is prepared as follows. N-Benzyloxycarbonyl-L-seryl-L-tyrosine [Z$_1$-Ser-Tyr(OH)] is reacted with glycine ethyl ester hydrochloride in the presence of N-hydroxysuccinimide, triethylamine, and dicyclohexylcarbodiimide in N,N-dimethylformamide to give Z$_1$-Ser-Tyr-Gly(OEt), which is next catalytically hydrogenated in the presence of hydrogen chloride to remove the Z$_1$ protecting group. The hydrogenation product, Ser-Tyr-Gly(OEt)HCl, is then reacted with pGlu-His-Trp(N$_3$), obtained from pGlu-His-Trp(NHNH$_2$) in the usual way,

in the presence of a base to give pGlu-His-Trp-Ser-Tyr-Gly(OEt), which is finally subjected to hydrazinolysis in a lower alkanol solvent to give the desired pGlu-His-Trp-Ser-Tyr-Gly(NHNH$_2$) intermediate.

L-Pyroglutamyl-L-histidyl-L-tryptophanyl-L-seryl-L-tyrosylglycyl-L-leucyl hydrazide, that is, the heptapeptide hydrazide of formula IV wherein $R_1$ is Tyr-Gly-Leu, is obtained from the following series of reactions. N-Benzyloxycarbonyl-L-seryl-L-tyrosyl hydrazide [$Z_1$-Ser-Tyr(NHNH$_2$)] is converted to the azide in the usual way, and the $Z_1$-Ser-Tyr(N$_3$) intermediate is reacted with glycyl-L-leucine methyl ester hydrochloride [Gly-Leu(OMe)HCl] in the presence of a base to give $Z_1$-Ser-Tyr-Gly-Leu(OMe). The $Z_1$-Ser-Tyr-Gly-Leu(OMe) intermediate is then catalytically hydrogenated in the presence of hydrogen chloride, and the hydrogenation product, Ser-Tyr-Gly-Leu(OMe)HCl, is reacted with pGlu-His-Trp(N$_3$) in the presence of a base to give pGlu-His-Trp-Ser-Tyr-Gly-Leu(OMe), which is finally reacted with hydrazine hydrate in a lower alkanol solvent to give the desired pGlu-His-Trp-Ser-Tyr-Gly-Leu(NHNH$_2$) intermediate.

The peptide compounds of formula III above, which together with their salts and certain intermediates used in their preparation are additional novel chemical intermediates of the invention, are prepared in a variety of ways. N$^G$-Nitro-L-arginyl-L-prolylglycinamide, that is, the tripeptide compound of formula III wherein $R_2$ represents NO$_2$Arg, salts thereof, and N-protected derivatives thereof are prepared as follows. An N-protected N$^G$-nitro-L-arginine derivative having the formula

$Z_2$-NO$_2$Arg(OH)   (VI)

is reacted with pentachlorophenol in the presence of dicyclohexylcarbodiimide to give an N-protected N$^G$-nitro-L-arginine pentachlorophenyl ester. This activated ester is next reacted with Pro-Gly(NH$_2$), obtained from the catalytic hydrogenation of $Z_1$-Pro-Gly(NH$_2$), to give an N-protected N$^G$-nitro-L-arginine-L-prolylglycinamide derivative having the formula

$Z_2$-NO$_2$Arg-Pro-Gly(NH$_2$)   (VII)

In formulas VI and VII above, $Z_2$ represents benzyloxycarbonyl, benzhydryloxycarbonyl, tert-butyloxycarbonyl, cyano-tert-butyloxycarbonyl, or 9-fluorenylmethoxycarbonyl. To obtain NO$_2$Arg-Pro-Gly(NH$_2$) or a salt thereof, the N-protecting group is removed from the derivative of formula VII by reaction with hydrogen bromide in glacial acetic acid or trifluoroacetic acid, reaction with ammonia in a lower alkanol, or reaction with trifluoroacetic acid.

L-Leucyl-N$^G$-nitro-L-arginyl-L-prolylglycinamide, that is, the tetrapeptide compound of formula III wherein $R_2$ represents Leu-NO$_2$Arg, salts thereof, and N-protected derivatives thereof are obtained as follows. An N-protected leucine pentachlorophenyl ester, prepared as described in detail hereinafter, is reacted with NO$_2$Arg-Pro-Gly(NH$_2$) to give an N-protected L-leucyl-N$^G$-nitro-L-arginyl-L-prolylglycinamide derivative having the formula

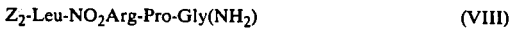

$Z_2$-Leu-NO$_2$Arg-Pro-Gly(NH$_2$)   (VIII)

where $Z_2$ has the same meaning as given above, and this derivative is converted into Leu-NO$_2$Arg-Pro-Gly(NH$_2$) or a salt thereof by removing the N-protecting group as described above for the N-protected derivative of formula VII.

Glycyl-L-leucyl-N$^G$-nitro-L-arginyl-L-prolyl-glycinamide, that is, the pentapeptide compound of formula III wherein $R_2$ represents Gly-Leu-NO$_2$Arg, salts thereof, and N-protected derivatives thereof are prepared by reacting an activated ester, such as the p-nitrophenyl ester or the pentachlorophenyl ester, of an N-protected glycine derivative, prepared as also described in detail hereinafter, with Leu-NO$_2$Arg-Pro-Gly(NH$_2$) to give an N-protected glycyl-L-leucyl-N$^G$-nitro-L-arginyl-L-prolylglycinamide derivative having the formula

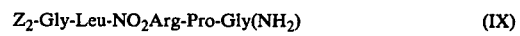

$Z_2$-Gly-Leu-NO$_2$Arg-Pro-Gly(NH$_2$)   (IX)

where $Z_2$ has the aforementioned significance, and then removing the N-protecting group from this derivative by utilizing the reactions given above for the N-protected derivative of formula VII.

The decapeptide nitro-LRF and certain intermediates for its preparation form acid-addition salts by reaction with a variety of inorganic and organic acids, including hydrochloric, hydrobromic, hydriodic, nitric, sulfuric, phosphoric, acetic, trifluoroacetic, benzoic, citric, and related acids. While the free base peptide compounds and their salts may differ somewhat in certain physical properties, such as solubility in polar solvents, they have in common a utility as chemical intermediates.

Certain of the peptide compounds of the invention can exist in anhydrous form and in solvated, including hydrated, forms. In general, the hydrated and solvated forms are useful as chemical intermediates in an equivalent manner to the anhydrous or unsolvated form.

The new peptide compounds of the invention are of value as chemical intermediates in the preparation of the luteinizing hormone releasing factor (LRF), which is a naturally-occurring decapeptide, identified chemically as L-pyroglutamyl-L-histidyl-L-tryptophanyl-L-seryl-L-tyrosylglycyl-L-leucyl-L-arginyl-L-prolyl-glycinamide, and represented by the formula

pGlu-His-Trp-Ser-Tyr-Gly-Leu-Arg-Pro-Gly(NH$_2$)   (X)

This decapeptide compound is obtained from the decapeptide nitro-LRF compound of the invention, represented by formula I above, by catalytic hydrogenation, as described in detail hereinafter.

The luteinizing hormone releasing factor (LRF) is known to be formed in the hypothalamus of mammals, from which it is released and transported by way of the hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. (For a report of the structure of LRF, which has also been referred to as luteinizing hormone releasing hormone, or LH-RH, and its biological activity, see Science, Vol. 174, No. 4008, Oct. 29, 1971, pages 511–512.)

The invention is illustrated by the following examples.

EXAMPLE 1

L-Pyroglutamyl-L-histidyl-L-tryptophanyl-L-seryl-L-tyrosyl hydrazide (a) To a suspension of 28 g. of L-pyroglutamyl-L-histidyl hydrazide in 800 ml. of dry N,N-dimethylformamide, cooled to −10° C., is added 235 ml. of 2.55 N hydrogen chloride in tetrahydrofuran (freshly prepared by bubbling hydrogen chloride into redistilled tetrahydrofuran). The mixture is stirred at −10° to −20° C. for 30 minutes, 19.1 ml. of isoamyl nitrite is added, and the resulting mixture is stirred for 90 minutes at −20° C. The mixture, which contains L-pyroglutamyl-L-histidyl azide, is then cooled to −30° C., and to it are added first 82.8 ml. of triethylamine, dropwise over a 15-minute period, then 25.5 g. of L-tryptophane methyl ester hydrochloride, and finally 14.0 ml. more of triethylamine, again dropwise. This reaction mixture is then stirred below −20° C. for one hour and at 0°–5° C. for 90 minutes and is kept in a refrigerator at −5° C. overnight. It is then filtered, and the filtrate is concentrated under reduced pressure at 40°–45° C. The semi-solid residue obtained is triturated with hot tetrahydrofuran and the solid L-pyroglutamyl-L-histidyl-L-tryptophane methyl ester product is isolated by filtration and dried in a vacuum oven at 50° C.; it is suitable for use without further purification.

(b) The L-pyroglutamyl-L-histidyl-L-tryptophane methyl ester obtained as described in (a) above (41.7 g.) is added with stirring to 1.5 liters of boiling methanol and the hot solution is filtered. After the filtered solution cools to room temperature, 50 ml. of 98% hydrazine hydrate is added, and the resulting mixture is kept at room temperature for 3 days. The solid product obtained, which is L-pyroglutamyl-L-histidyl-L-tryptophanyl hydrazide, is isolated by filtration, washed with methanol and with ether, and dried; m.p. 259°–260° C., following crystallization from water.

(c) To a mixture consisting of 4.16 g. of N-benzyloxycarbonyl-L-seryl-L-tyrosine methyl ester [for the preparation of this compound see J. Am. Chem. Soc., 76, 5076 (1954)], 30 ml. of methanol, and 416 mg. of 5% palladium-on-barium sulfate is added 8.7 ml. of methanol containing 400 mg. of hydrogen chloride, and hydrogen is passed over the stirred mixture for 75 minutes. The mixture is then filtered to remove the catalyst, and the filtrate is evaporated to dryness under reduced pressure to give a solid residue of L-seryl-L-tyrosine methyl ester hydrochloride, which is suitable for use without further purification.

(d) To a solution of 932 mg. of L-pyroglutamyl-L-histidyl-L-tryptophanyl hydrazide (prepared as described in (b) above) in a mixture of 8.4 ml. of dry N,N-dimethylformamide and 7.0 ml. of dimethyl sulfoxide, cooled to −12° C., is added dropwise 5.16 ml. of 2.325 N hydrogen chloride in tetrahydrofuran. The mixture is cooled to −20° C., 0.4 ml. of isoamyl nitrite is added, and the resulting mixture is stirred at −20° C. for 30 minutes. The mixture, which contains L-pyroglutamyl-L-histidyl-L-tryptophanyl azide, is cooled to −25° C., and to it are added first 1.96 ml. of triethylamine and then 636 mg. of L-seryl-L-tyrosine methyl ester hydrochloride (prepared as described in (c) above). The reaction mixture is stirred at −20° C. for 30 minutes and at 0° C. for 30 minutes and is stored in a refrigerator at −5° C. for 48 hours. It is then filtered and the filtrate is evaporated under reduced pressure. The residue is triturated with tetrahydrofuran, the mixture is stored in the refrigerator for 26 hours, and the solvent is decanted to give a residue of L-pyroglutamyl-L-histidyl-L-tryptophanyl-L-seryl-L-tyrosine methyl ester, which is dissolved in 20 ml. of methanol. To the solution is added 1 ml. of 99% hydrazine hydrate, and the mixture is stirred at room temperature overnight to give solid L-pyroglutamyl-L-histidyl-L-tryptophanyl-L-seryl-L-tyrosyl hydrazide, which is isolated by filtration and dried under reduced pressure; m.p. 215°–217° C., following crystallization from water; $[\alpha]_D^{25}$ −17° (1.01% in N,N-dimethylformamide).

EXAMPLE 2

L-Pyroglutamyl-L-histidyl-L-tryptophanyl-L-seryl-L-tyrosylglycyl hydrazide (a) To a stirred mixture consisting of 4.82 g. of N-benzyloxycarbonyl-L-seryl-L-tyrosine, 1.519 g. of N-hydroxysuccinimide, 1.675 g. of glycine ethyl ester hydrochloride, and 60 ml. of N,N-dimethylformamide, cooled to −15° C., is added first 1.68 ml. of triethylamine and then 2.48 g. of dicyclohexylcarbodiimide, and the resulting mixture is stirred at −15° C. for 2 hours and at room temperature for 25 hours. The mixture is then concentrated to remove solvent, and the residue is partitioned between dilute hydrochloric acid and ethyl acetate. The organic layer is separated, washed with saturated aqueous sodium chloride, with saturated aqueous sodium bicarbonate, and with saturated aqueous sodium chloride again, dried, and evaporated to give a solid residue of N-benzyloxycarbonyl-L-seryl-L-tyrosylglycine ethyl ester; m.p. 166°–169° C., following crystallization from ethyl acetate; $[\alpha]_D^{25}$ −23.2° (2% in methanol).

(b) A mixture consisting of 1.463 g. of N-benzyloxycarbonyl-L-seryl-L-tyrosylglycine ethyl ester, 30 ml. of methanol, 146 mg. of 5% palladium-on-carbon, and 2.6 ml. of 1.26 N hydrogen chloride in methanol is hydrogenated at one atmosphere and 25° C. for 95 minutes. The mixture is then filtered to remove the catalyst, and the filtrate is evaporated to dryness under reduced pressure to give an amorphous solid residue is L-seryl-L-tyrosylglycine ethyl ester hydrochloride; m.p. 191°–193° C., following crystallization from methanol-ether; $[\alpha]_D^{25}$ +10° (1% in methanol).

(c) To a stirred suspension of 1.165 g. of L-pyroglutamyl-L-histidyl-L-tryptophanyl hydrazide (prepared as described in Example 1(b) above) in 30 ml. of N,N-dimethylformamide, cooled to −20° C., is added 6.13 ml. of 2.45 N hydrogen chloride in tetrahydrofuran and 0.5 ml. of isoamyl nitrite, and the resulting mixture is stirred at −10° to −20° C. for one hour. The mixture, which contains L-pyroglutamyl-L-histidyl-L-tryptophanyl azide, is next cooled to −50° C. and to it are added first 2.1 ml. of triethylamine, then 975 mg. of L-seryl-L-tyrosylglycine ethyl ester hydrochloride (prepared as described in (b) above), and finally 0.35 ml. more of triethylamine. The stirred mixture is allowed to warm to 0° C. during one hour and is kept at −5° C. for 21 hours. It is then filtered, and the filtrate is evaporated under reduced pressure to give a residue of L-pyroglutamyl-L-histidyl-L-tryptophanyl-L-seryl-L-tyrosylglycine ethyl ester, which is dissolved in 50 ml. of methanol. To the solution is added 2 ml. of 99% hydrazine hydrate, and the resulting mixture is kept at room temperature for 16 hours. The solid that forms is isolated by filtration and stirred well with 20 ml. of water. The aqueous mixture is heated on the steam bath for 20 minutes, filtered, and the isolated solid is mixed with 15 ml. of methanol. The methanolic mixture is heated on the steam bath for 15 minutes, and the solid product is again isolated by filtration and dried. It is L-pyroglutamyl-L-histidyl-L-tryptophanyl-L-seryl-L-tyrosylglycyl hydrazide monohydrate; m.p. 218°–220° C.; $[\alpha]_D^{25}$ −22.7° (1% in 1 N hydrochloric acid).

EXAMPLE 3

L-Pyroglutamyl-L-histidyl-L-tryptophanyl-L-seryl-L-tyrosylglycyl-L-leucyl hydrazide (a) A mixture consisting of 3.65 g. of N-benzyloxycarbonylglycyl-L-leucine methyl ester [this compound is reported in Rec. trav. chim., 78, 487 (1959)], 50 ml. of methanol, 0.5 g. of 20% palladium-on-carbon, and 8.7 ml. of 1.25 N hydrogen chloride in methanol is hydrogenated at one atmosphere and room temperature for about 21 hours. The mixture is filtered, the filtrate is evaporated to dryness, and the oily residue is triturated with ether. The solid product obtained, which is glycyl-L-leucine methyl ester hydrochloride, is isolated and dried; m.p. 168°–170° C.; $[\alpha]_D^{25}$ −43.6° (2.02% in water).

(b) To a stirred solution of 7.49 g. of N-benzyloxycarbonyl-L-seryl-L-tyrosyl hydrazide [this compound is reported in Helv. Chim. Acta, 41, 1852 (1958)] in 50 ml. of N,N-dimethylformamide, cooled to −30° C., is first added 16.9 ml. of 3.607 N hydrogen chloride in tetrahydrofuran and then 2.7 ml. of isoamyl nitrite, and the resulting mixture is stirred at −30° C. for 30 minutes. The mixture, which contains N-benzyloxycarbonyl-L-seryl-L-tyrosyl azide, is next cooled to −60° C., and to it are added first 8.57 ml. of triethylamine, then 4.297 g. of glycyl-L-leucine methyl ester hydrochloride and finally 2.52 ml. more of triethylamine. The stirred mixture is allowed to warm to 0° C. during one hour and is stirred at 0° C. for one hour and kept at −5° C. for 48 hours. It is then filtered, and the filtrate is evaporated under reduced pressure at 40°–50° C. The gummy residue is partitioned between dilute hydrochloric acid and ethyl acetate, and the organic layer is separated, washed with saturated aqueous sodium bicarbonate and with saturated aqueous sodium chloride, dried, and evaporated to give a solid residue of N-benzyloxycarbonyl-L-seryl-L-tyrosylglycyl-L-leucine methyl ester; m.p. 166°–167° C., following two crystallizations from ethyl acetate-ether; $[\alpha]_D^{25}$ −25.4° (2% in N,N-dimethylformamide); $[\alpha]_D^{25}$ −38.2° (2.09% in methanol).

(c) A mixture consisting of 2.4 g. of N-benzyloxycarbonyl-L-seryl-L-tyrosylglycyl-L-leucine methyl ester, 60 ml. of methanol, 240 mg. of 5% palladium-on-carbon, and 5.4 ml. of 1.26 N hydrogen chloride in methanol is hydrogenated at one atmosphere and 25° C. for one hour. The mixture is then filtered to remove the catalyst, and the filtrate is evaporated to dryness under reduced pressure to give an amorphous solid residue of L-seryl-L-tyrosylglycyl-L-leucine methyl ester hydrochloride; $[\alpha]_D^{25}$ −12.9° (2% in methanol); $\lambda_{max}$ 278, $E_1^1$ 33.6 (methanol).

(d) To a suspension of 7.0 g. of L-pyroglutamyl-L-histidyl-L-tryptophanyl hydrazide (prepared as described in Example 1(b) above) in 180 ml. of N,N-dimethylformamide, cooled to −15° C., is added dropwise 36.5 ml. of 2.51 N hydrogen chloride in tetrahydrofuran. The mixture is cooled to −20° C., 3.04 ml. of isoamyl nitrite is added, and the resulting mixture is stirred at −20° C. for 30 minutes. The mixture, which contains L-pyroglutamyl-L-histidyl-L-tryptophanyl azide, is next cooled to −30° C., and to it are added first 14.84 ml. of triethylamine, dropwise, and then 7.34 g. of L-seryl-L-tyrosylglycyl-L-leucine methyl ester hydrochloride (prepared as described in (c) above). The reaction mixture is stirred at −20° C. for 30 minutes and at 0° C. for 2 hours and is then stored in the refrigerator at −5° C. overnight. It is then filtered, and the filtrate is evaporated. The residue is triturated with 250 ml. of tetrahydrofuran, and after 3 hours at room temperature, the solid residue of L-pyroglutamyl-L-histidyl-L-tryptophanyl-L-seryl-L-tyrosylglycyl-L-leucine methyl ester is isolated by filtration and dissolved in 650 ml. of methanol. The methanolic solution is treated with activated charcoal and filtered, and to the filtrate is added 15.0 ml. of 99% hydrazine hydrate. The resulting mixture is kept at room temperature for 3 days, and the solid that forms is isolated and mixed with 200 ml. of ether. After 2 days at room temperature, the ethereal mixture is filtered, and the isolated solid is mixed with 360 ml. of methanol. The methanolic mixture is heated to boiling for 5 minutes, kept at room temperature for 10 minutes, and filtered to give a solid product, which is washed with methanol and with ether and dried. It is L-pyroglutamyl-L-histidyl-L-tryptophanyl-L-seryl-L-tyrosylglycyl-L-leucyl hydrazide dihydrate; m.p. 213°–215° C.; $[\alpha]_D^{25}$ −21.2° (1.93% in a 1:1 mixture of N,N-dimethylformamide and dimethyl sulfoxide).

EXAMPLE 4

$N^G$-Nitro-L-arginyl-L-prolylglycinamide, salts, and N-protected derivatives.

(a) To a stirred mixture consisting of 11 g. of $N^G$-nitro-L-arginine, 6 g. of magnesium oxide, and 100 ml. of water is added a solution of 16 g. of benzhydrylazidoformate [this compound is reported in J. Am. Chem. Soc., 87, 3969 (1965)] in 100 ml. of dioxane, and the resulting mixture is stirred at room temperature for 18 hours. It is then filtered, and the filtrate is concentrated to remove the dioxane. The aqueous concentrate is acidified with solid citric acid, and the acidified mixture is extracted with ethyl acetate. The extract is dried and concentrated to small volume, and the concentrate is diluted with ether to give a precipitate of N-benzhydryloxycarbonyl-$N^G$-nitro-L-arginine, which is isolated and dried; m.p. 65°–75° C.; $[\alpha]_D^{25}$ −2.6° (1% in methanol). To a mixture consisting of 10 g. of this intermediate product, 6.3 g. of pentachlorophenol, and 100 ml. of ethyl acetate, at 5° C., is added 5 g. of dicyclohexylcarbodiimide, and the resulting mixture is kept at 5° C. for 4 hours and then filtered. The filtrate is evaporated to remove the solvent, and the oily residue is crystallized from ethanol-water to give solid N-benzhydryloxycarbonyl-$N^G$-nitro-L-arginine pentachlorophenyl ester; m.p. 110°–115° C.; $[\alpha]_D^{25}$ −19.5° (1% in methanol).

(b) To a mixture consisting of 8.5 g. of N-tert-butyloxycarbonyl-$N^G$-nitro-L-arginine [this compound is reported in J. Am. Chem. Soc., 87, 620 (1965)], 14.4 g. of pentachlorophenol, and 300 ml. of methylene chloride, at 5° C., is added 6.2 g. of dicyclohexylcarbodiimide, and the resulting mixture is stirred at 5° C. for one hour and then allowed to warm to room temperature over 15 hours. The mixture is filtered and the isolated solid is washed with 500 ml. of ethyl acetate. The combined washings and filtrate are evaporated, the residue is dissolved in ethyl acetate, and the solution is filtered. The filtrate is washed successively with 100 ml. of 10% aqueous citric acid, 100 ml. of 1 N sodium hydrogen carbonate, and 100 ml. of saturated aqueous sodium chloride, dried, and evaporated to dryness to give a semisolid residue of N-tert-butyloxycarbonyl-$N^G$-nitro-L-arginine pentachlorophenyl ester; m.p. 112°–116° C., following crystallization from ethyl acetate-n-hexane; $[\alpha]_D^{25}$ −23.1° (1% in methanol).

(c) To a mixture consisting of 15.5 g. of $N^G$-nitro-L-arginine, 7.5 g. of sodium carbonate, and 200 ml. of water, at 5° C., is added, over 30 minutes, 10 g. of cyano-tert-butylchloroformate [reported in Chem. Ber., 104, 2427 (1971)], and the resulting solution is stirred at 10° C. for two hours. It is then washed with ether, acidified with 2 N sulfuric acid and extracted with ethyl acetate. The extract is dried and evaporated to dryness to give a residue of N-(cyano-tert-butyloxycarbonyl)-$N^G$-nitro-L-arginine; m.p. 144°–145° C., following crystallization from ethyl acetate-ethanol-ether; $[\alpha]_D^{25}$ −3° (2% in methanol). To a solution of 6 g. of this intermediate product in 30 ml. of N,N-dimethylformamide, at 5° C., is added 4.7 g. of pentachlorophenol and 3.6 g. of dicyclohexylcarbodiimide and the resulting mixture is kept at 5° C. for 18 hours. It is then filtered, and the filtrate is evaporated to dryness to give a residue of N-(cyano-tert-butyloxycarbonyl)-$N^G$-nitro-L-arginine pentachlorophenyl ester, which is triturated with ether, isolated, and dried; m.p. 196°–197° C.; $[\alpha]_D^{25}$ −21.3° (1% in N,N-dimethylformamide).

(d) To a mixture consisting of 8.7 g. of $N^G$-nitro-L-arginine, 4.3 g. of sodium carbonate, and 200 ml. of water, cooled to 0° C., is added a solution of 5.0 g. of 9-fluorenylmethylchloroformate [this compound is reported in J. Am. Chem. Soc., 92, 5748 (1970)] in 200 ml. of tetrahydrofuran, and the resulting mixture is stirred at 0° C. for one hour and at room temperature for 3 hours. The mixture is then acidified with 3 N hydrochloric acid and concentrated to remove the solvent. The residue is extracted with ethyl acetate, and the extract is washed with 100 ml. of 10% hydrochloric acid and with 100 ml. of water, dried, and evaporated to dryness to give a residue of N-9-fluorenylmethoxycarbonyl-$N^G$-nitro-L-arginine; m.p. 88°–96° C., following crystallization from ethyl acetate-n-hexane; $[\alpha]_D^{25}$ +3.22° (1.023% in methanol). To a mixture consisting of this intermediate product (5.4 g.), 10.6 g. of pentachlorophenol, and 200 ml. of N,N-dimethylformamide, cooled to 0° C., is added 2.8 g. of dicyclohexylcarbodiimide, and the resulting mixture is kept at 4° C. for 4 days. It is then filtered, and the filtrate is poured into 4 liters of water to give a precipitate of N-9-fluorenylmethoxycarbonyl-$N^G$-nitro-L-arginine pentachlorophenyl ester, which is isolated, washed with ether, and dried; m.p. 138°–142° C.

(e) A mixture consisting of 33.5 g. of N-benzyloxycarbonyl-L-prolylglycinamide (this compound has been reported in *Synthetic Peptides*, Vol. 1, G. R. Pettit, Van Nostrand Reinhold Company, New York, 1970, page 151), 1 g. of 20% palladium-on-carbon, and 500 ml. of methanol is hydrogenated at 50 lbs./in.$^2$ hydrogen pressure and room temperature for one hour. The mixture is filtered to remove the catalyst, and the filtrate is evaporated to dryness to give a solid residue of L-prolylglycinamide; m.p. 124°–127° C., following crystallization from acetonitrile-toluene; $[\alpha]_D^{25}$ −48.5° (2% in water).

(f) To a suspension of 12 g. of L-prolylglycinamide in 600 ml. of dioxane is added 43 g. of N-benzyloxycarbonyl-$N^G$-nitro-L-arginyl pentachlorophenyl ester (this compound is reported in *Synthetic Peptides*, op. cit., page 17), and the resulting mixture is stirred for 24 hours at 25°–30° C. or until a clear solution is obtained. The solution is then evaporated to remove the solvent, and the oily residue is washed three times with ether and three times with ethyl acetate to give a solid product, which is N-benzyloxycarbonyl-$N^G$-nitro-L-arginyl-L-prolylglycinamide; m.p. 100°–105° C., following crystallization from acetonitrile-ethyl acetate-ether; $[\alpha]_D^{25}$ −35.8° (1% in methanol).

(g) To a solution of 10 g. of N-benzhydryloxycarbonyl-$N^G$-nitro-L-arginine pentachlorophenyl ester (prepared as described in (a) above) in 200 ml. of dioxane is added 2.5 g. of L-prolylglycinamide, and the resulting mixture is stirred at 30°–35° C. for 18 hours and at 70°–75° C. for 3 hours. The mixture is then concentrated to about 50 ml., and the concentrate is diluted with ether to give a precipitate of N-benzhydryloxycarbonyl-$N^G$-nitro-L-arginyl-L-prolylglycinamide, which is isolated, washed with ether, and dried; m.p. 145°–150° C., following crystallization from 2-propanol; $[\alpha]_D^{25}$ −38° (1% in methanol).

(h) A mixture consisting of 3.1 g. of L-prolylglycinamide, 10.2 g. of N-tert-butyloxycarbonyl-$N^G$-nitro-L-arginine pentachlorophenyl ester (prepared as described in (b) above, and 300 ml. of dioxane is stirred at room temperature for 15 hours and at 50° C. for 2 hours. It is then filtered, and the filtrate is evaporated to dryness to give a solid residue of N-tert-butyloxycarbonyl-$N^G$-nitro-L-arginyl-L-prolylglycinamide; m.p. 158°–162° C., following crystallization from acetonitrile; $[\alpha]_D^{25}$ −37.8° (1.042% in methanol).

(i) To a solution of 33 g. of N-(cyano-tert-butyloxycarbonyl-$N^G$-nitro-L-arginine pentachlorophenyl ester (prepared as described in (c) above) in 800 ml. of dioxane is added 9.5 g. of L-prolylglycinamide, and the resulting mixture is stirred at 30°–35° C. for 3 days. The clear solution obtained is concentrated to about 100 ml., and the solid N-(cyano-tert-butyloxycarbonyl)-$N^G$-nitro-L-arginyl-L-prolylglycinamide that precipitates is isolated and crystallized from 2-propanol; m.p. 135°–140° C.; $[\alpha]_D^{25}$ −26.6° (1% in N,N-dimethylformamide).

(j) A mixture consisting of 3.15 g. of L-prolylglycinamide, 12.7 g. of N-9-fluorenylmethoxycarbonyl-$N^G$-nitro-L-arginine pentachlorophenyl ester (prepared as described in (d) above), and one liter of dioxane is stirred at room temperature for 15 hours and filtered. The filtrate is evaporated to dryness to give a solid residue of N-9-fluorenylmethoxycarbonyl-$N^G$-nitro-L-arginyl-L-prolylglycinamide; m.p. 125°–130° C. (softening at 100° C.), following crystallization from 2-propanol; $[\alpha]_D^{25}$ −42° (1.03% in methanol).

(k) Anhydrous ammonia is passed through a solution of 1.0 g. of N-9-fluorenylmethoxycarbonyl-$N^G$-nitro-L-arginyl-L-prolylglycinamide (prepared as described in (j) above) in 100 ml. of methanol for 10 minutes, and the resulting solution is kept at room temperature for 12 hours. The solution is then evaporated to remove the solvent, and the residue is dissolved in water. The aqueous mixture is extracted with ether and the ether extract is discarded. The aqueous phase is filtered, and the filtrate is evaporated to dryness to give a solid residue of $N^G$-nitro-L-arginyl-L-prolylglycinamide; m.p. 95°–104° C.; $[\alpha]_D^{25}$ −29.6° (1.01% in water).

(l) To a stirred solution of 1.01 g. of N-benzyloxycarbonyl-$N^G$-nitro-L-arginyl-L-prolylglycinamide (prepared as described in (f) above) in 7.74 ml. of glacial acetic acid, cooled in an ice bath, is added dropwise 6.26 ml. of 5.03 N hydrogen bromide in acetic acid, and the resulting mixture is stirred at room temperature for one hour. The mixture is then poured with stirring into 100 ml. of ether, and the solid $N^G$-nitro-L-arginyl-L-prolyl-glycinamide hydrobromide that precipitates is isolated by centrifugation and decantation of the supernatant liquid. It is purified as follows. It is mixed well with ether and separated by centrifugation and decantation four times, dried overnight under reduced pressure, dissolved in 20 ml. of methanol, and reprecipitated from the methanol solution with 80 ml. of ether. The methanol-ether mixture is cooled overnight in the refrigerator, filtered, and the isolated $N^G$-nitro-L-arginyl-L-prolylglycinamide hydrobromide is dried under reduced pressure; hydroscopic solid; $\lambda_{max}$ 269 m$\mu$, $E_1^1$ 247 (1 N hydrochloric acid).

(m) N-Benzhydryloxycarbonyl-$N^G$-nitro-L-arginyl-L-prolylglycinamide (3 g.; prepared as described in (g) above) is added to 10 ml. of trifluoroacetic acid at 0° C. The solid quickly dissolves with the evolution of a gas. After 5 minutes, 100 ml. of ether is added, and the solid $N^G$-nitro-L-arginyl-L-prolylglycinamide trifluoroacetate salt that precipitates is isolated, washed well with ether, and dried. The salt melts over the range 130°–160° C. with slow decomposition; $[\alpha]_D^{25}$ −8.4° (1% in methanol).

EXAMPLE 5

L-Leucyl-$N^G$-nitro-L-arginyl-L-prolylglycinamide, salts, and N-protected derivatives.

(a) To a mixture consisting of 13.1 g. of L-leucine, 6 g. of magnesium oxide, and 150 ml. of water is added a solution of 25.3 g. of benzhydrylazidoformate in 150 ml. of dioxane, and the resulting mixture is stirred at room temperature for 2 days. It is then filtered, and the filtrate is concentrated to remove the dioxane. The aqueous concentrate is acidified with solid citric acid, and the acidified mixture is extracted with ethyl acetate. The extract is dried and evaporated to dryness to give an oily residue of N-benzhydryloxycarbonyl-L-leucine, which is suitable for use without further purification. To a mixture of 32 g. of this intermediate product, 25 g. of pentachlorophenol, and 300 ml. of ethyl acetate, at 5° C., is added 20 g. of dicyclohexylcarbodiimide, and the resulting mixture is kept at 5° C. for 5 hours and filtered. The filtrate is concentrated to small volume, and the concentrate is treated with petroleum ether to give a precipitate of N-benzhydryloxycarbonyl-L-leucine pentachlorophenyl ester, which is isolated and crystallized from ethanol-water; m.p. 84°–86° C.; $[\alpha]_D^{25}$ −27.8° (2% in methanol).

(b) To a mixture consisting of 19.4 g. of L-leucine, 15.7 g. of sodium carbonate, and 500 ml. of water, cooled to 0° C., is added a solution of 19.1 g. of 9-fluorenylmethylchloroformate in 200 ml. of tetrahydrofuran, and the resulting mixture is stirred at 0° C. for one hour and at room temperature for 15 hours. The mixtue is then acidified with 3 N hydrochloric acid and concentrated to remove the solvent. The residue is extracted with ethyl acetate, and the extract is washed with 100 ml. of 10% hydrochloric acid and with 100 ml. of water, dried, and evaporated to dryness to give a residue of N-9-fluorenylmethoxycarbonyl-L-leucine, which is slurried with n-hexane, isolated, and dried; m.p. 76°–79° C.; $[\alpha]_D^{25}$ −28.7° (1.01% in methanol). To a mixture consisting of 15.2 g. of this intermediate product, 37 g. of pentachlorophenol, and 300 ml. of N,N-dimethylformamide, cooled to 5° C., is added 9.8 g. of dicyclohexylcarbodiimide, and the resulting mixture is kept at 4° C. for 2 days. It is then filtered, and the filtrate is evaporated to dryness to give a residue of N-9-fluorenylmethoxycarbonyl-L-leucine pentachlorophenyl ester, which is triturated with n-hexane, isolated and dried; m.p. 119°–121° C.; $[\alpha]_D^{25}$ −35.4° (1.00% in methanol).

(c) Into a solution of 33 g. of N-benzyloxycarbonyl-$N^g$-nitro-L-arginyl-L-prolylglycinamide (prepared as described in Example 4(f) above) in 250 ml. of glacial acetic acid at 15°–20° C. is bubbled 40 g. of hydrogen bromide, and the resulting solution is kept at room temperature for 2 hours and then poured, with vigorous stirring, into 2 liters of ether. The solid that precipitates, which is $N^G$-nitro-L-arginyl-L-prolylglycinamide hydrobromide, is isolated, washed well with ether, dried for 18 hours under reduced pressure, and dissolved in 150 ml. of N,N-dimethylformamide. The solution is cooled to 5° C., and 20 g. of triethylamine is added. After 5 minutes, the mixture is filtered to remove triethylamine hydrobromide, and the isolated solid is washed with 20 ml. of N,N-dimethylformamide. To the combined washings and filtrate is added 25 g. of N-benzyloxycarbonyl-L-leucine p-nitrophenyl ester, and the resulting mixture is stirred at room temperature for 24 hours. The mixture is then evaporated to remove the solvent, and the residue is washed three times with ether and three times with ethyl acetate to give a solid product, which is N-benzyloxycarbonyl-L-leucyl-$N^G$-nitro-L-arginyl-L-prolylglycinamide; m.p. 135°–140° C. (softening at 120° C.), following three crystallizations from 2-propanol; $[\alpha]_D^{25}$ −50° (1% in methanol).

(d) To a suspension of 2.5 g. of $N^G$-nitro-L-arginyl-L-prolylglycinamide trifluoroacetate salt (prepared as described in Example 4(m) above) in 200 ml. of dioxane at room temperature is added 1.5 ml. of triethylamine, and after 3 to 5 minutes, 3 g. of N-benzhydryloxycarbonyl-L-leucine pentachlorophenyl ester (prepared as described in (a) above). The resulting mixture is stirred and heated at 30°–35° C. for 18 hours and at 70° C. for 5 hours, and is evaporated to dryness to give a residue of N-benzhydryloxycarbonyl-L-leucyl-$N^G$-nitro-L-arginyl-L-prolylglycinamide, which is triturated with ether, isolated, and dried; m.p. 135°–140° C.; $[\alpha]_D^{25}$ −48.4° (1% in methanol).

(e) To a suspension of 1.8 g. of $N^G$-nitro-L-arginyl-L-prolylglycinamide trifluoroacetate salt (prepared as described in Example 4(m) above) in 300 ml. of dioxane is added 0.85 g. of N-ethylmorpholine, and the mixture is stirred at room temperature for 15 minutes. N-tert-Butyloxycarbonyl-L-leucine pentachlorophenyl ester [1.77 g.; this compound is reported in J. Org. Chem., 33, 4521 (1968)] is then added, and the mixture is stirred at room temperature for 30 minutes more and diluted with 100 ml. of methanol. The methanolic mixture is stirred at room temperature for 15 hours and at 70° C. for 7 hours, filtered, and the filtrate is evaporated. The residue is dissolved in 100 ml. of acetonitrile and to the solution is added 500 ml. of ether. The solid that precipitates is isolated and dissolved in 600 ml. of chloroform. The chloroform solution is washed with 100 ml. of saturated aqueous sodium chloride, dried, and evaporated to dryness. The residue is dissolved in methanol, the methanolic solution is filtered, and the filtrate is treated with activated charcoal and evaporated to give a solid residue of N-tert-butyloxycarbonyl-L-leucyl- $N^G$-nitro-L-arginyl-L-prolylglycinamide; m.p. 140°–145° C.; $[\alpha]_D^{25}$ −58.4° (1.00% in methanol).

(f) A mixture consisting of 0.16 g. of N-9-fluorenylmethoxycarbonyl-L-leucine pentachlorophenyl ester (prepared as described in (b) above), 0.1 g. of $N^G$-nitro-L-arginyl-L-prolylglycinamide, and 200 ml. of N,N-dimethylformamide is stirred at room temperature for 2 days, filtered, and the filtrate evaporated to dryness to give a residue of N-9-fluorenylmethoxycarbonyl-L-leucyl-$N^G$-nitro-L-arginyl-L-prolylglycinamide, which is purified by chromatography on silica gel; the product is eluted with methanol-benzene (15:85); m.p. 117°–119° C.

(g) Into a solution of 8 g. of N-benzyloxycarbonyl-L-leucyl-$N^G$-nitro-L-arginyl-L-prolylglycinamide (prepared as described in (c) above) in 100 ml. of glacial acetic acid, at 15°–20° C., is bubbled 10 g. of hydrogen bromide, and the resulting solution is kept at room temperature for 2 hours and then poured, with stirring, into one liter of ether. The precipitated solid, which is L-leucyl-$N^G$-nitro-L-arginyl-L-prolylglycinamide hydrobromide, is isolated, washed well with ether, and dried under reduced pressure. The salt product is dissolved in methanol, and to the solution is added a sufficient quantity of a strongly basic quaternary ammonium polystyrene type anion exchange resin, such as, for example, Amberlite IRA 410, to neutralize the salt, as indicated by a negative silver nitrate test for halogen. The mixture is then filtered to remove the resin, and the filtrate is evaporated to dryness to give L-leucyl-$N^G$-nitro-L-arginyl-L-prolylglycinamide, obtained as an oil that could not be crystallized.

(h) Anhydrous ammonia is passed through a solution of 0.073 g. of N-9-fluorenylmethoxycarbonyl-L-leucyl-$N^G$-nitro-L-arginyl-L-prolylglycinamide (prepared as described in (f) above) in 20 ml. of methanol for 5 minutes, and the resulting solution is kept at room temperature for 12 hours and evaporated. The residue is dissolved in water, the aqueous solution is washed with ether and filtered, and the filtrate is evaporated to dryness to give L-leucyl-$N^G$-nitro-L-arginyl-L-prolylglycinamide.

(i) Trifluoroacetic acid (5 ml.) is added dropwise to 0.3 g. of N-tert-butyloxycarbonyl-L-leucyl-$N^G$-nitro-L-arginyl-L-polylglycinamide (prepared as described in (e) above), and after 10 minutes at room temperature, 500 ml. of ether is added to give a solid precipitate of L-leucyl-$N^G$-nitro-L-arginyl-L-prolylglycinamide trifluoroacetate salt, which is isolated, washed with 500 ml. of ether, and dried; m.p. 143°–153° C.; $[\alpha]_D^{25}$ −29° (1.01% in methanol).

EXAMPLE 6

Glycyl-L-leucyl-$N^G$-nitro-L-arginyl-L-prolylglycinamide, salts, and N-protected derivatives (a) To a mixture consisting of 10 g. of N-benzhydryloxycarbonylglycine [this compound is reported in J. Am. Chem. Soc., 87, 3969 (1965)], 9.4 g. of pentachlorophenol, and 150 ml. of ethyl acetate, at 5° C., is added 7.3 g. of dicyclohexylcarbodiimide, and the resulting solution is kept at 5° C. for 5 hours and filtered. The filtrate is evaporated, and the residue is triturated with petroleum ether to give a solid precipitate of N-benzhydryloxycarbonylglycine pentachlorophenyl ester, which is isolated and dried; m.p. 171°–172° C.

(b) Into a solution of 7 g. of N-benzyloxycarbonyl-L-leucyl-$N^G$-nitro-L-arginyl-L-prolylglycinamide (prepared as described in Example 5(c) above) in 100 ml. of glacial acetic acid at 15° C. is bubbled 10 g. of hydrogen bromide, and the resulting solution is kept at room temperature for 2 hours and then poured, with stirring, into one liter of ether. The precipitated solid, which is L-leucyl-$N^G$-nitro-L-arginyl-L-prolylglycinamide hydrobromide, is isolated, washed well with ether, dried under reduced pressure, and dissolved in 75 ml. of N,N-dimethylformamide. The solution is cooled to 10° C., and 5 g. of triethylamine is added. After 5 minutes, the mixture is filtered, and to the filtrate is added 3.7 g. of N-benzyloxycarbonylglycine p-nitrophenyl ester (this compound is reported in *Synthetic Peptides*, op. cit., page 42). The resulting solution is stirred at room temperature for 24 hours and evaporated to dryness. The residue is washed three times with ether and three times with ethyl acetate to give solid N-benzyloxycarbonylglycyl-L-leucyl-$N^G$-nitro-L-arginyl-L-prolylglycinamide, which is isolated and dried; m.p. 150° C. (softening at 140° C.), following crystallization from dioxane; $[\alpha]_D^{25}$ −45° (1% in methanol).

(c) To a suspension of 3 g. of L-leucyl-$N^G$-nitro-L-arginyl-L-prolylglycinamide trifluoroacetate salt (prepared as described in Example 5(i) above) in a mixture of 200 ml. of dioxane and 50 ml. of N,N-dimethylformamide is added first 1.5 ml. of triethylamine and then 2.7 g. of N-benzhydryloxycarbonylglycine pentachlorophenyl ester (prepared as described in (a) above), and the resulting mixture is stirred at 30°–35° C. for 48 hours. The mixture is then evaporated and the residue is triturated with ether to give a solid precipitate of N-benzhydryloxycarbonylglycyl-L-leucyl-$N^G$-nitro-L-arginyl-L-prolylglycinamide, which is isolated, washed with ether and with water, and dried; m.p. 145°–150° C., following crystallization from 2-propanol; $[\alpha]_D^{25}$ −46.8° (1% in methanol).

(d) To a suspension of 3.0 g. of L-leucyl-$N^G$-nitro-L-arginyl-L-prolylglycinamide trifluoroacetate salt (prepared as described in Example 5(i) above) in 500 ml. of dioxane is added 1.0 g. of N-ethylmorpholine, and the mixture is stirred at room temperature for 15 minutes. N-tert-Butyloxycarbonylglycine pentachlorophenyl ester [2.5 g.; this compound is reported in J. Org. Chem., 33, 4521 (1968)] is then added, and the mixture is stirred at room temperature for 3 days and filtered. The filtrate is evaporated, the residue is dissolved in 100 ml. of acetonitrile, and to the solution is added 500 l ml. of ether. The solid that precipitates is isolated and dissolved in 600ml. of chloroform. The chloroform solution is washed with 100 ml. of saturated aqueous sodium chloride, dried, and evaporated. The residue is mixed well with 100 ml. of methanol, the methanolic mixture is filtered, and the filtrate is evaporated to give a solid residue of N-tert-butyloxycarbonylglycyl-L-leucyl-$N^G$-nitro-L-arginyl-L-prolylglycinamide, which is isolated and dried; m.p. 132°–137° C.; $[\alpha]_D^{25}$ −54° (1.01% in methanol).

(e) Into a stirred solution of 940 l mg. of N-benzyloxycarbonylglycyl-L-leucyl-$N^G$-nitro-L-arginyl-L-prolylglycinamide (prepared as described in (b) above) in 20 ml. of trifluoroacetic acid, cooled to 0° C. in an ice-salt bath, is bubbled hydrogen bromide for one hour, and the mixture is stirred at 0° C. for 30 minutes. It is then evaporated under reduced pressure and the residue is triturated with ether. The ethereal mixture is centrifuged, the liquid is decanted, and the ether treatment is repeated twice more to give solid glycyl-L-leucyl-$N^G$-nitro-L-arginyl-L-prolylglycinamide hydrobromide, which is isolated and dried. The salt product is dissolved in methanol, and the solution is neutralized with a strongly basic anion exchange resin, such as Amberlite IRA 410. The mixture is then filtered, and the filtrate is evaporated to give glycyl-L-leucyl-$N^G$-nitro-L-arginyl-L-prolylglycinamide, obtained as an oil that could not be crystallized.

(f) N-Benzhydryloxycarbonylglycyl-L-leucyl-$N^G$-nitro-L-arginyl-L-prolylglycinamide (1.5 g.; prepared as described in (c) above) is mixed with 5 ml. of trifluoroacetic acid at 5° C. The solid quickly dissolves with the evolution of a gas, and after 3 minutes, 50 ml. of ether is added to give a solid precipitate of glycyl-L-leucyl-$N^G$-nitro-L-arginyl-L-prolylglycinamide, trifluoroacetate salt, which is isolated, washed with ether, and dried; m.p. 170°-180° C.; $[\alpha]_D^{25}$ −32.8° (2% in methanol).

EXAMPLE 7

L-Pyroglutamyl-L-histidyl-L-tryptophanyl-L-seryl-L-tyrosylglycyl-L-leucyl-$N^G$-nitro-L-arginyl-L-prolylglycinamide. (Nitro-LRF).

Preparation I:

To a stirred solution of 1.546 g. of L-pyroglutamyl-L-histidyl-L-tryptophanyl-L-seryl-L-tyrosylglycyl hydrazide (prepared as described in Example 2 above) in 20 ml. of N,N-dimethylformamide, cooled to −30° C., is first added 3.51 ml. of 3.42 N hydrogen chloride in tetrahydrofuran and then 0.4 ml. of isoamyl nitrite, and the resulting mixture is stirred at −30° C. for 30 minutes. The mixture, which contains L-pyroglutamyl-L-histidyl-L-tryptophanyl-L-seryl-L-tyrosylglycyl azide, is next cooled to −55° C., and to it are added first 1.68 ml. triethylamine and then a solution of 970 mg. of L-leucyl-$N^G$-nitro-L-arginyl-L-prolylglycinamide (prepared as described in Example 5(g) above) in 9 ml. of N,N-dimethylformamide. The stirred mixture is allowed to warm at 0° C. during one hour and is kept at −5° C. for 24 hours. It is then filtered, and the filtrate is evaporated to dryness. The residue is dissolved in 40 ml. of methanol, and the methanolic solution is poured with stirring into 200 ml. of ethyl acetate to give a solid precipitate of nitro-LRF, which is isolated by filtration, washed with ethyl acetate and with ether and dried. This solid product is subjected chromatography on silica gel using chloroform-methanol-water (60:45:10) as the eluant, and the residue obtained upon evaporation of the eluant fractions is triturated with ethanol to give a pale yellow solid, which is isolated and dried under reduced pressure at 60° C. It is nitro-LRF monohydrate; m.p.: decomposes at 179°-186° C.; $[\alpha]_D^{25}$ −31.7° (2% in N,N-dimethylformamide). Further purification of the product is carried out as follows. It is again subjected to chromatography on silica gel, this time using chloroform-methanol-water-acetic acid (60:45:3:7) as the eluant. The combined solids isolated from the best fractions as determined by this layer chromatography are then subjected to chromatography on a column of hydroxypropylated dextran gel (Sephadex LH-20), which is eluted with chloroform-methanol-water (60:45:10). The solid residues obtained upon evaporation of the best fractions are combined, dissolved in dilute acetic acid and the solution is lyophilized to give L-pyroglutamyl-L-histidyl-L-tryptophanyl-L-seryl-L-tyrosylglycyl-L-leucyl-$N^G$-nitro-L-arginyl-L-prolylglycinamide monoacetate tetrahydrate; m.p.: decomposes at 175°-185° C.

Preparation II:

To a stirred solution of 923 mg. of L-pyroglutamyl-L-histidyl-L-tryptophanyl-L-seryl-L-tyrosylglycyl-L-leucyl hydrazide dihydrate (prepared as described in Example 3 above) in a mixture of 5.2 ml. of N,N-dimethylformamide and 3.5 ml. of dimethyl sulfoxide, cooled to −15° C., is added 2.44 ml. of 2.47 N hydrogen chloride in tetrahydrofuran. The mixture is cooled to −20° C., 0.21 ml. of isoamyl nitrite is added, and the resulting mixture is stirred at −20° C. for 30 minutes. The mixture, which contains L-pyroglutamyl-L-histidyl-L-tryptophanyl-L-seryl-L-tyrosylglycyl-L-leucyl azide, is then cooled to −25° C., and to it are added first 1.03 ml. of triethylamine, dropwise, and then a solution of 482 mg. of $N^G$-nitro-L-arginyl-L-prolylglycinamide hydrobromide (prepared as described in Example 4(l) above) in 3 ml. of N,N-dimethylformamide. This reaction mixture is stirred at −20° C. for 30 minutes and at 0° C. for 2 hours and is kept in a refrigerator at −5° C. for 24 hours. It is then filtered, the filtrate is evaporated, and the residue is triturated with tetrahydrofuran. After 24 hours, the tetrahydrofuran mixture is filtered, and the isolated solid is dissolved in 50 ml. of methanol. The methanolic solution is treated with 400 mg. of activated charcoal and filtered through diatomaceous silica (Hyflo Supercel can be used). The filtrate is concentrated to a volume of 30 ml. and chilled overnight to give solid nitro-LRF, which is isolated and dried; $\lambda_{max}$ 271, $E_1^1$ 148 (1 N hydrochloric acid). The solid product is dissolved in dilute acetic acid, and the solution is lyophilized to give L-pyroglutamyl-L-histidyl-L-tryptophanyl-L-seryl-L-tyrosylglycyl-L-leucyl-$N^G$-nitro-L-arginyl-L-prolylglycinamide monoacetate tetrahydrate, after drying under reduced pressure at 35° C. Upon further drying under reduced pressure at 100° C., the product is nitro-LRF monoacetate dihydrate.

Preparation III:

To a solution of 880 mg. of L-pyroglutamyl-L-histidyl-L-tryptophanyl-L-seryl-L-tyrosyl hydrazide (prepared as described in Example 1 above) in 35 ml. of dry N,N-dimethylformamide, cooled to −10° C., is added 3.0 ml. of 2.40 N hydrogen chloride in tetrahydrofuran. The mixture is cooled to −20° C., 0.24 ml. of isoamyl nitrite is added, and the resulting mixture is stirred at −20° C. for 30 minutes. The mixture, which contains L-pyroglutamyl-L-histidyl-L-tryptophanyl-L-seryl-L-tyrosyl azide, is then cooled to −25° C., and to it are added first 1.2 ml. of triethylamine, dropwise, and then 805 mg. of glycyl-L-leucyl-$N^G$-nitro-L-arginyl-L-prolylglycinamide hydrobromide (prepared as described in Example 6(e) above). This reaction mixture is stirred at −20° C. for 30 minutes and at 0°-5° C. for 2 hours and is kept in a refrigerator at −5° C. overnight. It is then filtered, the filtrate is evaporated, and the residue is triturated with tetrahydrofuran and the solvent decanted. The second residue is dissolved in 40 ml. of methanol, 20 ml. of absolute ethanol is added, and the mixture is chilled overnight to give a solid precipitate of nitro-LRF, which is isolated and dried. The solid product thus obtained is further purified by chromatography on silica gel using chloroform-methanol-water (60:45:5) as the eluant. The solid obtained upon evaporation of the eluate is then dissolved in dilute acetic acid and the solution is lyophilized to give L-pyroglutamyl-L-histidyl-L-tryptophanyl-L-seryl-L-tyrosylglycyl-L-leucyl-$N^G$-nitro-L-arginyl-L-prolylglycinamide monoacetate tetrahydrate, which is shown by thin layer chromatographic analysis to be identical with that obtained in Prepartion II above.

EXAMPLE 8

L-Pyroglutamyl-L-histidyl-L-tryptophanyl-L-seryl-L-tyrosylglycyl-L-leucyl-L-arginyl-L-prolylglycinamide. (LRF)

A mixture consisting of 900 mg. of L-pyroglutamyl-L-histidyl-L-tryptophanyl-L-seryl-L-tyrosylglycyl-L-leucyl-$N^G$-nitro-L-arginyl-L-prolylglycinamide (nitro-LRF: prepared as described in Example 7 above), 30 ml. of 10% glacial acetic acid in methanol, and 900 mg. of 20% palladium-on-carbon is shaken at room temperature with hydrogen at an initial pressure of 50 lbs./in.$^2$ for 48 hours or until the nitro-LRF starting material is no longer detected by thin layer chromatography of a sample of the reaction mixture. The mixture is filtered to remove the catalyst and the filtrate is lyophilized to give somewhat crude solid LRF. This crude product is purified as follows. It is first subjected to chromatography on a column of silica gel (Brinkman), which is developed successively with chloroform-methanol (60:45), chloroform-methanol-water (60:45:5 and 60:45:10), and chloroform-methanol-water-acetic acid (60:45:10:1). The solids isolated from the best fractions as determined by thin layer chromatography are combined and subjected to partition chromatography on a column of hydroxypropylated dextran gel (Sephadex LH-20), using the lower layer of a n-butanol-water-acetic acid mixture (8:40:4) as the stationary phase and developing with n-butanol-water-acetic acid (80:25:9.5). The solids obtained upon evaporation of the best fractions are dissolved in dilute acetic acid and the solution is lyophilized to give a solid product determined by elemental analysis to be L-pyroglutamyl-L-histidyl-L-tryptophanyl-L-seryl-L-tyrosylglycyl-L-leucyl-L-arginyl-L-prolylglycinamide diacetate trihydrate; molecular weight, 1356.5; $[\alpha]_D^{25}$ −57.0° (1% in 1% acetic acid).

We claim:

1. A peptide hydrazide compound represented by the formula

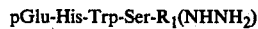

where $R_1$ represents a member of the class consisting of Tyr, Tyr-Gly, and Tyr-Gly-Leu.

2. A compound according to claim 1 which is L-pyroglutamyl-L-histidyl-L-tryptophanyl-L-seryl-L-tyrosyl hydrazide.

3. A compound according to claim 1 which is L-pyroglutamyl-L-histidyl-L-tryptophanyl-L-seryl-L-tyrosylglycyl hydrazide.

4. A compound according to claim 1 which is L-pyroglutamyl-L-histidyl-L-tryptophanyl-L-seryl-L-tyrosylglycyl-L-leucyl hydrazide.

* * * * *